United States Patent [19]

Bron

[11] Patent Number: 5,101,854
[45] Date of Patent: Apr. 7, 1992

[54] LOW-OUTPUT FLOW REGULATOR

[76] Inventor: Dan Bron, 36 Palmach Street, Haifa, Israel

[21] Appl. No.: 549,935

[22] Filed: Jul. 9, 1990

[30] Foreign Application Priority Data

Jul. 12, 1989 [IL] Israel .................................. 90950

[51] Int. Cl.⁵ .................................. G05D 7/01
[52] U.S. Cl. .................................. 137/501
[58] Field of Search .................................. 137/501, 504

[56] References Cited

U.S. PATENT DOCUMENTS

| 3,886,968 | 6/1975 | Murrel | 137/501 |
| 4,209,133 | 6/1980 | Mehoudar | 137/501 X |
| 4,241,757 | 12/1980 | Bron | 137/501 |
| 4,343,305 | 8/1982 | Bron | 137/501 X |
| 4,428,397 | 1/1984 | Bron | 137/501 X |
| 4,508,140 | 4/1985 | Harrison | 137/501 |
| 4,769,012 | 9/1988 | Quang | 137/504 X |

FOREIGN PATENT DOCUMENTS 0018088 10/1980 European Pat. Off. .
2369615 10/1977 France .
2560770 9/1985 France .

Primary Examiner—Robert G. Nilson
Attorney, Agent, or Firm—Larson and Taylor

[57] ABSTRACT

A low-output flow regulator, including a housing, having an inlet aperture through which a liquid from a liquid source may enter, the inlet aperture is adapted to at least indirectly communicate with a consumer of the liquid, the housing comprises a raised portion with a recessed top surface provided with an opening leading at least indirectly to the consumer, and the raised portion has a circumferential wall surface projecting into the housing. The regulator further includes a cup-shaped elastomeric diaphragm consisting of a relatively thin and, in its position of rest, substantially plane active portion, and an annular wall portion integral with the active portion. The diaphragm is mounted on the raised portion, thereby dividing the housing into an inlet chamber and an outlet chamber, the inside surface of the annular wall portion defines in conjunction with the circumferential wall surface of the raised portion a flow-attenuating passageway for the liquid, and the passageway connects the inlet chamber with the outlet chamber.

10 Claims, 4 Drawing Sheets

LOW-OUTPUT FLOW REGULATOR

The present invention relates to a flow regulator, more particularly to a low-output flow regulator. It also relates to a disposable auto-syringe or infusor using such a flow regulator.

Flow regulators, in the presently used sense, are devices that, connected to a source of liquid, will produce a constant output, in spite of possible changes of pressure at that source and/or at the consumer end.

Flow regulators of that kind, which work on the principle of maintaining a constant pressure differential across an elastomeric diaphragm, are well-known in the art. In the earlier ones of these regulators, these diaphragms were peripherally clamped onto their seats. While regulators of this type have more or less satisfactory service as along as relatively large outputs (1-4 liter/h) were concerned and with very moderate demands for accuracy such as encountered in e.g., drip irrigation emitters, it turned out that for lower outputs, such as prevailing in. e.g., infusion sets (0.5-3 ml/min) and with narrower tolerances, these diaphragms were no longer reliable. This, as was found out, was due to the mounting method-by clamping which, because of the compressed clamping zone that tended to uncontrollably squeeze the diaphragm material inwards, thereby unpredictably and irreproducibly forming a bulge and changing the elastic properties of the diaphragm as mounted.

Attempts were made to overcome this problem by having the disk-shaped diaphragms freely rest on the edges of their circular seat without being clamped thereto. This proved to be a substantial improvement and facilitated the successful use of diaphragm-type flow regulators also for the above-mentioned low outputs of general infusion sets.

These freely resting diaphragms suffer, however, from another drawback: They are stressed not by stretching, but in flexing, which deleteriously affects their sensitivity to small and/or slow changes in pressure thereby introducing hysteresis effects.

Still lower outputs—at smaller tolerances—are, however, required for the infusing of premature babies and the newborn, and for the administration of patients of all ages and over extended periods of time, of certain types of medications. Here, outputs needed vary between 0.5 and 2.5 ml/h, at a tolerance of about 5%. These demands are far beyond the capabilities of all present day diaphragm-type flow regulators and so far could only be met by so-called syringe pumps which are intricate and very expensive electro-mechanical devices.

The known prior art methods of sealing the flow attenuating passageways are not applicable for low-output flow regulators of the instant invention since, a) even small changes in the tolerances of a rigid plastic covering element of the passageway, not to mention even the slightest deformation that such an element acquires in time, cause "short circuit" flow between sections of the passageway, and b) the covering of the attenuating passageway with a rubber diaphragm pressed thereon causes uneven protrusions of diaphragm portions into the passageway, resulting in a non-uniform cross sectional area throughout the entire length of the passageway.

It is one of the objects of the present invention to overcome the drawbacks and limitations of prior-art flow regulators of the diaphragm-type and to provide a flow regulator that, at a cost not, or not substantially, exceeding the cost or prior-art flow regulators of the diaphragm type, will produce volumetric outputs as low as 0.5-2.5 ml/h at a tolerance not exceeding 5% and over extended periods of time.

It is further object of the present invention to provide a low-output flow regulator in which the flow attenuating passageway is sealed by means of a slightly stretched membrane made of rubber or the like.

It is a further object of the invention to provide a disposable auto-syringe using a flow regulator according to the invention, which permits the full potential of these flow regulators to be realized and, at a more fraction of the daily cost of a syringe pump, provides a device capable of rendering most services obtained from one of the above-mentioned syringe pumps.

According to the invention, there is therefore provided a low-output flow regulator, comprising a housing, having an inlet aperture through which a liquid from a liquid source may enter, said inlet aperture being adapted to at least indirectly communicate with a consumer of said liquid, said housing including a raised portion with a recessed top surface provided with an opening leading at least indirectly to said consumer, said raised portion having a circumferential wall surface and projecting into the housing, and a cup-shaped elastomeric diaphragm consisting of a relatively thin and, in its position of rest, substantially plane active portion, and an annular wall portion integral with said active portion, said diaphragm being mounted on said raised portion, thereby dividing said housing into an inlet chamber and an outlet chamber, the inside surface of said annular wall portion defining in conjunction with the circumferential wall surface of said raised portion a flow-attenuating passageway for said liquid, said passageway connecting said inlet chamber with said outlet chamber.

While the flow regulator according to the invention is eminently suitable for the above-mentioned medical purposes, this does by no means exclude its usefulness for other tasks such as, e.g. drip irrigation emitters.

According to a further aspect of the invention, there is provided a disposable auto-syringe comprising syringe-body means fillable at least by aspiration with a liquid to be infused, to which body means is connectable a flow regulator capable of producing a constant liquid output regardless of fluctuations of pressure brought to bear on the liquid in said syringe-body means, syringe-piston means arranged to be acted upon by forces tending to push said piston means into said body means to the effect of displacing said aspirated liquid from said body means, and elastic restoring means arranged to act on said piston means and tending to restore said piston means from a position in which it is remote from the output end of said syringe to a position in which it is closer to said output end.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
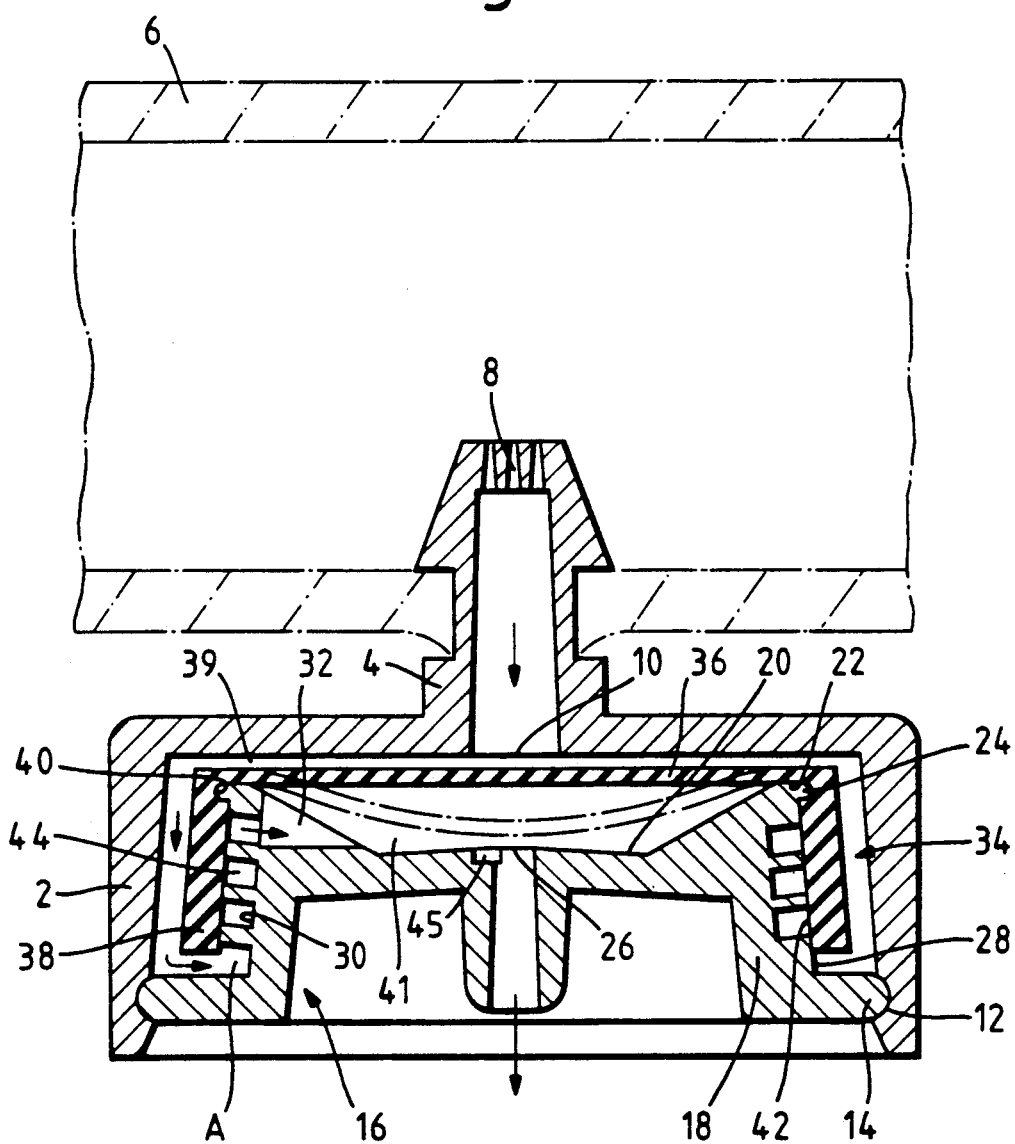
FIG. 1 is a cross-sectional view of a first embodiment of the fixed-output type flow regulator according to the invention.

Referring now to the drawings, there is seen a first embodiment of the flow regulator according to the invention, consisting of a split housing comprising a first housing part 2 having a connector 4 with a "barbed" tip which serves to retain the connector 4 once it has been pushed into a hole in, say, a tube 6 carrying a liquid. The liquid reaches the inside of the housing via a strainer 8 and an inlet aperture 10.

At the lower end of the cup-shaped housing part 2 there is provided a groove 12 into which, upon assembly, snaps over the flange-like rim 14 of a second housing part 16. The latter has a raised portion 18 integral with the rim 14. The raised portion has a recessed top surface 20 which produces a relatively narrow peripheral edge 22. Also seen is a circumferential head or lip 24 the purpose of which will be explained further below. In the center of the top surface 20 there is provided an opening 26 which leads to the consumer.

The raised portion 18, in assembly, projects into the hollow of the first housing part 2 and has a circumferential wall surface 28 in which is provided a helically spiralling groove 30 staring on the left side, right above the rim flange 14 (arrow A) and ending after several turns, leading into a slot 32, thus communicating with the space above the recessed surface 20.

In the embodiment shown in FIG. 1, the wall surface 28 is slightly conical, which facilitates both manufacturing and mounting, but it could also be cylindrical.

Further seen is a cup-shaped diaphragms 34 make of a high-quality elastomer such as silicone rubber or the like. It is seen to consist of a relatively thin (0.3-0.5 mm) and, in its position of rest, substantially plane, active portion 36 and, integral with the latter, a heavier wall portion 38.

It is this design by which the aforementioned problems of diaphragm-mounting are overcome, and which enables the flow regulators of the present invention to be used for the extremely low flow rates of 0.5-2.5 ml/hr (at a tolerance of 5%), at which the known diaphragm flow regulators are quite useless.

As is clear from the drawing, the diaphragm 34 is mounted on the raised portion 18 of the second housing part 16. The relative dimensions of the diaphragm and of the circumferential wall surface 28 of the raised portion 18 are such that, when mounted, the diaphragm 34 is slightly stretched, thereby also assuring satisfactory sealing and uniform working thereof. For securing the diaphragm to the raised portion, a circumferential undercut 40 is provided along the corner of the inside surface 42 of the diaphragm wall portion 38, into which undercut, upon assembly, snaps the above-mentioned circumferential lip 24. The mounted diaphragm divides the housing into an inlet chamber 39 and an outlet chamber 41.

It is also clearly seen that the above inside surface 42 of the diaphragm wall portion 38, in conjunction with the circumferential wall surface 28 of the raised portion 18, turn the open grooves 30 on that wall portion into a continuous, enclosed passageway 44 such that, in order to reach the slot 32, a liquid particle entering the passageway 44 at point A must pass the entire length of that spiralling duct, along which flow attenuation takes place. The grooves 30, however, can also be provided in the inside surface 42 of the diaphragm wall portion 38, as seen in the variant of FIG. 2, where the flow-attenuating passageway 44 is again defined by cooperation between the above inside surface and the circumferential wall surface 28 of the raised portion 18.

Figure 2:
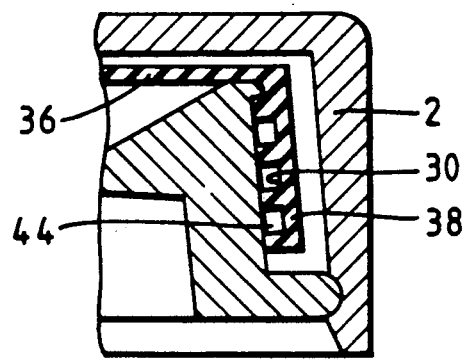
FIG. 2 is a partial cross-sectional view of a variant of the embodiment of FIG. 1.

Although both FIGS. 1 and 2 show flow-attenuating passageways 44 in the form of helically spiralling ducts, these passageways can also have the shape of meandering labyrinth-type ducts.

In FIG. 1 the regulator is shown to be of the type used as a drip irrigator in which the cross-sectional area of the ducts are relatively large for providing a suitable flow-rate.

The connector 4 could also be of the female type that fits the tip of a syringe, in which case the ducts will be configured to have smaller dimensions.

The operational principle of these flow regulators is well-known and does not require elaboration. Due to the continuous outflow of liquid through the passageway 44 of the regulator, a pressure differential is created across the diaphragm 34 (higher pressure in the inlet chamber 39, lower pressure in the output chamber 41) which causes the diaphragm to bulge (see dash-dotted lines in FIG. 1) and, by approaching the opening 26, to restrict the effective cross section thereof and, thus reduce outflow. Reduced outflow, in turn, will increase pressure in the outlet chamber. This pressure increase, assisted by the elastic restoring force of the diaphragm itself, will reduce the bulge, thereby again increasing outflow. The diaphragm 34 thus oscillates about what is known as "set point" of the regulator at which it achieves its rated output, i.e. the point at which a balance is achieved between the bulge-causing pressure differential upon the diaphragm, and the bulge-reducing elastic restoring force of the diaphragm material.

the flow regulator of FIG. 1 is of the "fixed output" type i.e. its volumetric output is predetermined and cannot be adjusted or varied. To vary the regulator output without changing the diaphragm is only possible by changing diaphragm working amplitude, i.e. the possible height or depth of bulging.

Figure 3:
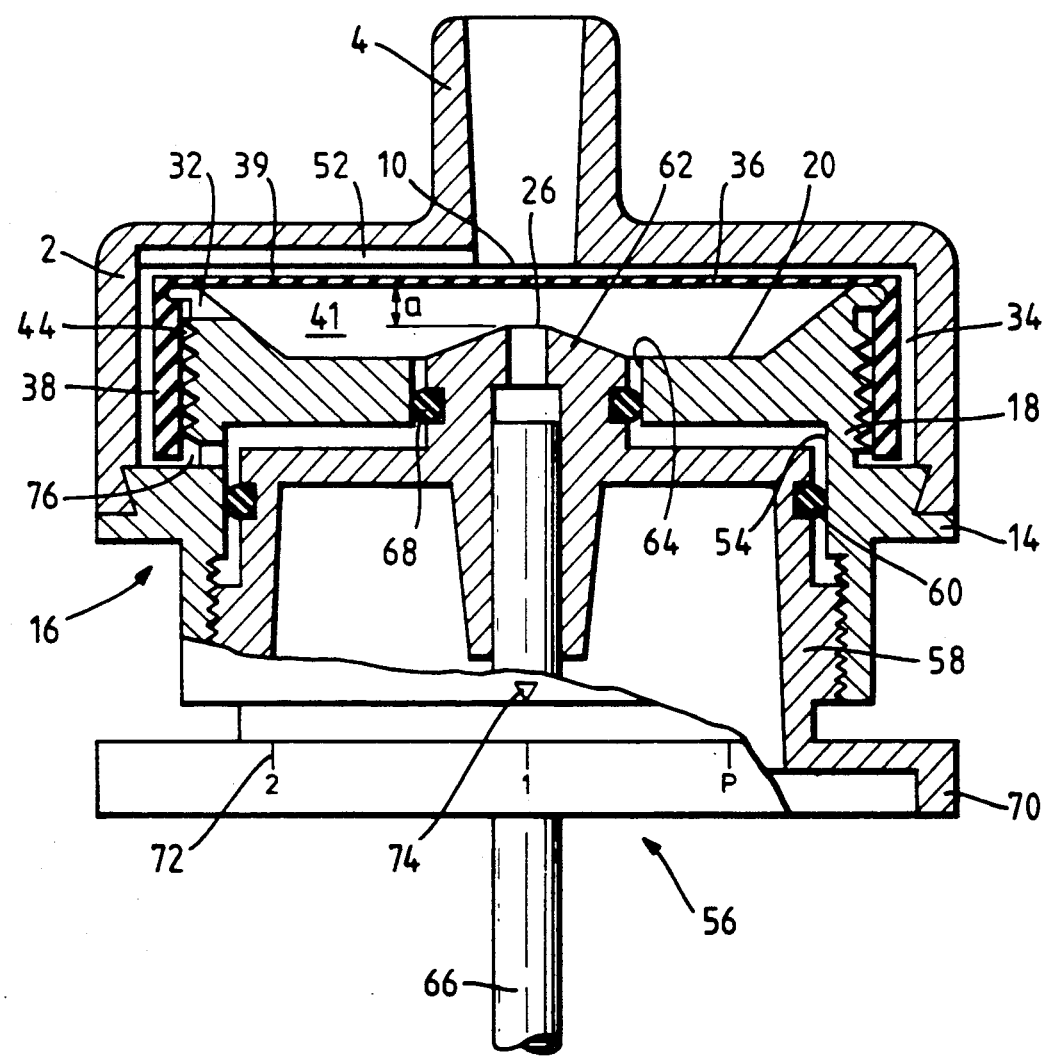
FIG. 3 illustrates, the partial cross-section, a second embodiment of a variable-output flow regulator according to the invention.

A more complex embodiment of a variable-output flow regulator according to the invention is shown in FIG. 3. The first housing part 2 differs from that of FIG. 1 mainly in two details: the connector 4 is now of the female type that fits the top of a standard syringe, and there is provided a radial groove 52 leading from the inlet aperture 10 to the inside wall of the cup-shaped housing part 2. The purpose of this groove will become apparent further below.

The second housing part 16 of this embodiment is of greater height, projecting, as it does, beyond the first housing part 2. It is provided with a relatively deep recess 54, a portion of the internal wall of which carries an internal thread.

There is further seen a output-adjusting member 56 comprising a body portion 58 provided over a section of its axial extent with an external thread which matches the internal thread of the second housing part 16 and, by being rotated relative to the second housing part 16, can move axially inside the latter. A first O-ring 60 permits the body portion 58 to move inside the recess 54, while sealing off the clearance between the body portion 58 and the recess 54.

There is also seen a central projection 62, axially extending from, and integral with, the body portion 58. This projection protrudes into an enlarged opening 64 of the recessed surface 20 and is provided with an opening 26 which, in this case, via a length of plastic tubing 66, leads, e.g., to a cannula to be inserted into a patient's vein. A second O-ring 68 seals off the clearance between the projection 62 and the opening 64 in the recessed top surface 20.

From what has been explained so far, it is clear that by a rotary movement of the body portion 58, the distance a between the diaphragm and the opening 26, that is, the working amplitude of the diaphragm and, thus, it will be remembered, the output of the flow regulator, can be adjusted or varied.

However, mere variability at these low outputs (e.g. one drop every three minutes) would be quite useless unless means are provided that would not only indicate the output set, but would ensure reproducibility.

The lower rim 70 of the adjusting member 56 thus carries a scale 72 which, in conjuction with an index mark 74 provided on the lower edge of the second housing point 16, indicates settings representing a range of regulator outputs obtainable.

One of the scale marks denoted by the letter P for "priming" indicates a position of the adjusting member 56 in which it has been drawn out to such a degree that the O-ring 68 no longer seals off the relatively large clearance between the projection 62 and the opening 64 in the recessed top surface 20. There is furthermore provided a bypass aperture 76 which enables the inlet chamber 39 to communicate with the outlet chamber 41 while bypassing the flow-attenuating passageway 44.

This is important in the "priming" stage when, for instance, the tubing 66 must be rapidly filled from a syringe to which the flow regulator is attached. Conversely, it may be necessary to fill the syringe by suction via the tubing. (This suction operation also explains the need for the radial groove 52: without such a groove, suction by the syringe which draws the diaphragm 34 up against the connector inlet aperture 10 would cause the diaphragm to practically seal off this opening, not permitting liquid to enter the syringe). As it is, the radial groove 52 lets liquid pass even when the diaphragm is drawn up against the inlet aperture 10. After priming, the adjustment member 56 is again screwed in, up to the scale mark denoting the desired output.

When the embodiment of FIG. 3 is used as an in-line flow-regulator in an infusion set, the groove 52 is not needed. Indeed it is advantageous to slightly raise the edge of the inlet aperture 10 to form an annular bead-like rim to facilitate the use of the diaphragm 34 as non-return valve, preventing backflow of blood from the vein into the infusion bag, should the latter accidentally come to be located at a level below that of the hypodermic needle.

Figure 4:
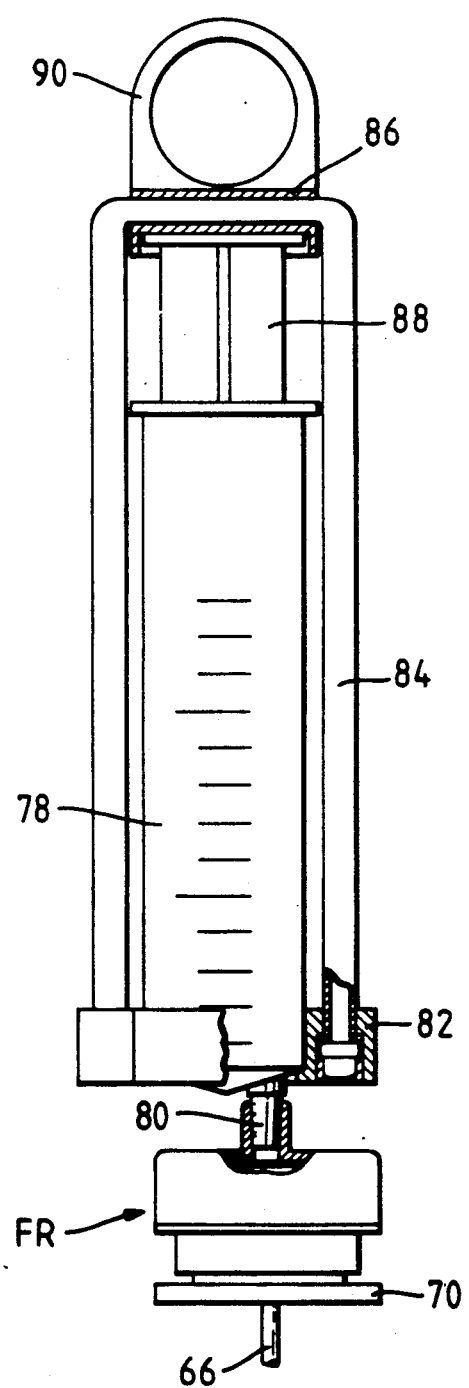
FIG. 4 represents a preferred embodiment of an auto-syringe to be used in conjunction with a flow regulator according to the invention.

FIG. 4 represents a disposable auto-syringe according to the invention, designed to operate in conjunction with the flow regulator FR shown in FIG. 3.

There is seen a syringe body 78, advantageously of a regular disposable syringe, comprising a standard male connector 80 and a ring 82 to which are anchorable the suitably shaped ends of a rubber band 84 led through a head piece 86 accommodating the upper end of the syringe piston 88 and provided with a pulling ring 90. The plastic tubing 66 leads to the patient to be infused.

In operation, the auto-syringe is either directly filled or filled through the flow regulator (the latter being set to "P" (priming)) by inserting the hypodermic needle or cannula at the end of the plastic tubing 66 into the bottle containing the liquid to be infused and drawing up the piston 88. When filled to the desired volume, the rim 70 of the adjusting member is set to the desired scale value, the rubber band is stretched with the aid of ring 90, the head piece 86 is mounted on the piston 88, and the syringe is ready for use. The elastically stretched rubber band 84 will push down the piston 88 and although the force exerted by it on the piston is not uniform, being strongest at the beginning of the infusion period and gradually dropping off, the flow regulator FR according to the invention will take care of this nonuniformity and produce a uniform, constant outflow.

For interruption or termination of infusion, the ring 90 is pulled up and aside.

The rubber band 84 could obviously be replaced by a single, or two separate, helical tension springs.

Figure 5:
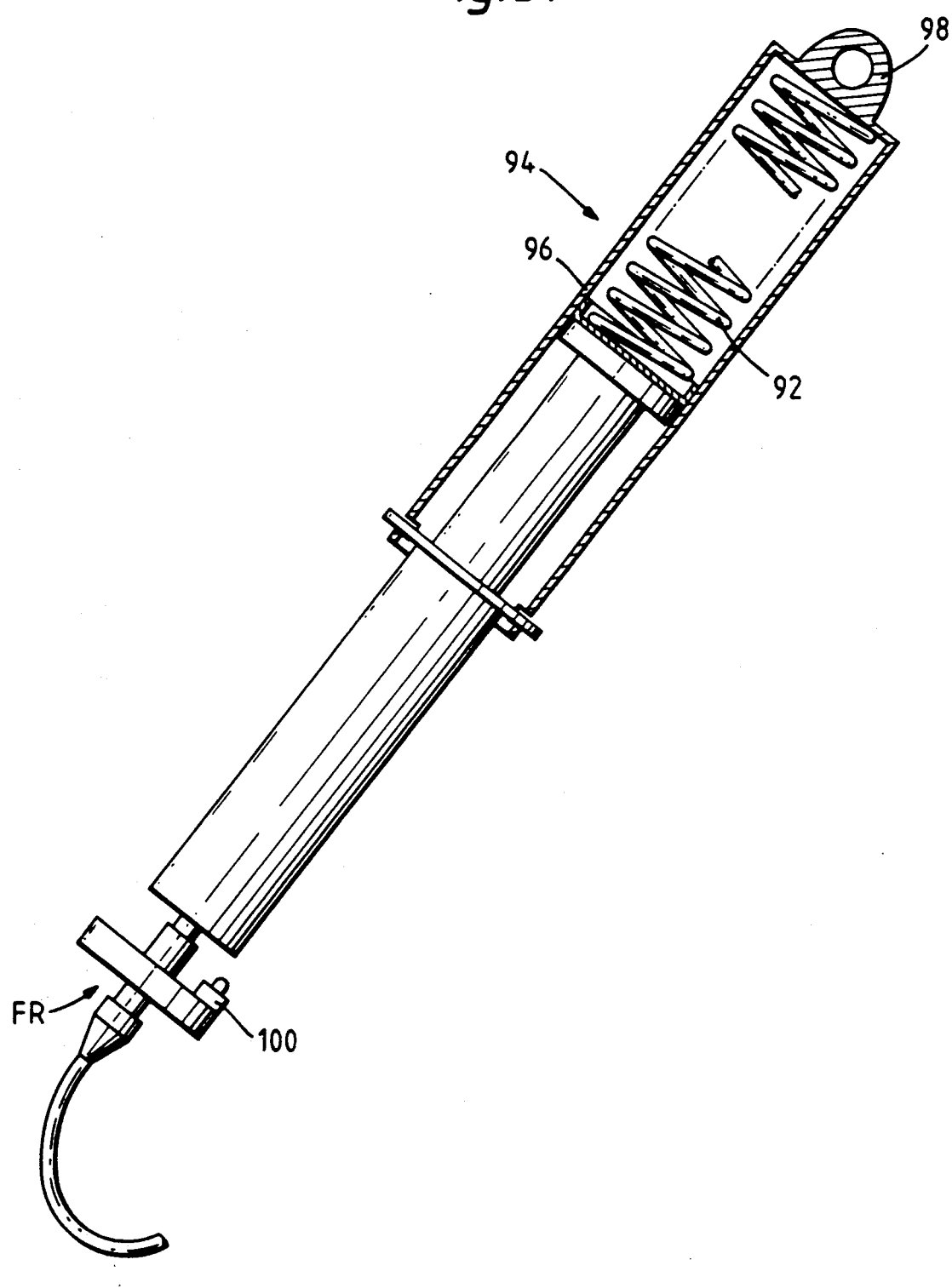
FIG. 5 shows a syringe activator as used in conjunction with a standard disposable syringe and a flow regulator according to the invention.

FIG. 5 represents another embodiment, in which a compression spring 92 is located outside of a regular disposable syringe, as part of an activator 94 that is re-usable. The activator housing 96 can be snapped onto the flange of the syringe body and is provided with a lug 98 whereby it can be suspended from an infusion stand.

The flow regulator is of the fixed-output type and is provided with an air release valve 100 actuated manually.

An optional feature of the regulator illustrated in FIG. 1 is a relatively narrow, shallow and short recess 45 leading into the opening 26 and preferably having a rectangular cross section in a plane perpendicular to the paper. The purpose of this recess is to enhance constancy of output, in particular, to prevent a falling-off of the output at higher pressures.

It would also be possible to make the flow regulator of either FIG. 1 or 3 an integral part of the syringe body 78 (FIG. 5) by removing the bottom of the body 78 and liquid-tightly attaching the second housing part 16 of the regulator to end portion of the body 84.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A low-output flow regulator, comprising:
   a split housing, including a first housing part having an inlet aperture through which a liquid from a liquid source may enter and which at least indirectly communicates with a consumer of said liquid. and a second housing part including a raised portion with a recessed top surface provided with an opening leading at least indirectly to said consumer, said raised portion having a circumferential wall surface and projecting into said first housing part, and a cup-shaped elastomeric diaphragm comprising a relatively thin and, in its position of rest, substantially planar active portion, and an annular wall portion integral with said active portion, said diaphragm being mounted on said raised portion, thereby dividing said split housing into an inlet chamber and an outlet chamber, the inside surface of said annular wall portion defining in conjunction with the circumferential wall surface of said raised portion a flow-attenuating passageway for said liquid, said passageway connecting said inlet chamber with said outlet chamber.

2. The flow regulator as claimed in claim 1, wherein said cup-shaped diaphragm is slightly stretched and secured to said raised portion by a circumferential undercut along the corner of the inside surface of said diaphragm wall portion into which, upon assembly, snaps a circumferential lip projecting from the edge of said wall surface of said raised portion.

3. The flow regulator as claimed in claim 1, wherein said flow-attentuating passageway is in the form of a helically spiraling duct.

4. The flow regulator as claimed in claim 1, wherein said passageway is defined by a flow-attenuating groove provided in the circumferential wall surface of said raised portion in conjunction with the inside surface of said annular wall of said cup-like diaphragm.

5. The flow regulator as claimed in claim 1, wherein said passageway is defined by a flow-attenuating groove provided in the inside surface of said annular wall of said cup-like diaphragm in conjunction with the circumferential wall surface of said raised portion.

6. The flow regulator as claimed in claim 1, further comprising means to vary the distance between said diaphragm in its position of rest and the effective axial location of said opening in said recessed top surface and, thereby, to adjust the output of said regulator.

7. The flow regulator as claimed in claim 6, wherein said means comprises an output-adjusting member axially movably and liquid-tightly accommodated in said housing, said adjusting member being provided with a substantially central aperture leading to said consumer, wherein said adjusting member, when axially moved relative to said housing, causes the distance between said opening and said diaphragm in its position of rest to be varied, thereby adjusting the output of said regulator.

8. The flow regulator as claimed in claim 7, wherein said output-adjusting member comprises a body portion provided over a section of its axial extent with an external thread engageable in a matching internal thread provided inside a recess in said second housing part, said body portion thus being axially moveable therein by rotating it relatively thereto, first sealing means sealing off a clearance between the nonthreaded sections of said body portion and said recess in said second housing part, and further comprising a central projection, axially extending from, and integral with, said body portion and protruding into said opening in said recessed top surface, second sealing means sealing off a clearance between said projection and said opening in said recessed top surface, said projection being provided with a substantially central aperture leading to said consumer.

9. The flow regulator as claimed in claim 8, further comprising a scale which, in conjunction with an index mark, indicates settings representing a range of regulator outputs obtainable.

10. The flow regulator as claimed in claim 8, wherein said second sealing means is fully withdrawable from said opening in said recessed top surface, thereby providing a bypass via which said liquid is free to flow in either direction without having to pass through said flow-attenuating passageway.

* * * * *